US012056830B2

(12) United States Patent
Cvetko et al.

(10) Patent No.: US 12,056,830 B2
(45) Date of Patent: Aug. 6, 2024

(54) AUGMENTING REAL-TIME VIEWS OF A PATIENT WITH THREE-DIMENSIONAL DATA

(71) Applicant: Novarad Corporation, American Fork, UT (US)

(72) Inventors: Steven Cvetko, Draper, UT (US); Wendell Arlen Gibby, Mapleton, UT (US)

(73) Assignee: Novarad Corporation, Provo, UT (US)

( * ) Notice: Subject to any disclaimer, the term of this patent is extended or adjusted under 35 U.S.C. 154(b) by 0 days.

(21) Appl. No.: 17/972,489

(22) Filed: Oct. 24, 2022

(65) Prior Publication Data

US 2023/0038130 A1    Feb. 9, 2023

Related U.S. Application Data

(63) Continuation of application No. 17/316,222, filed on May 10, 2021, now Pat. No. 11,481,987, which is a
(Continued)

(51) Int. Cl.
*G06T 19/00* (2011.01)
*A61B 5/00* (2006.01)
(Continued)

(52) U.S. Cl.
CPC .......... *G06T 19/006* (2013.01); *A61B 5/0015* (2013.01); *A61B 5/0071* (2013.01);
(Continued)

(58) Field of Classification Search
None
See application file for complete search history.

(56) References Cited

U.S. PATENT DOCUMENTS 9,538,962 B1    1/2017  Hannaford
10,028,727 B2 *  7/2018  Inoue .................. G06T 15/80
(Continued)

FOREIGN PATENT DOCUMENTS

WO    WO 2015/008470    1/2015

OTHER PUBLICATIONS

Justin Barad: "Controlling Augmented Reality in the Operating Room: A Surgeon's Perspective", Medgadget, Oct. 30, 2015, 4 pages, Retrieved from the Internet: URL:https://www.medgadget.com/2015/10/controlling-augmented-reality-operating-room-surgeons-perspective.html.

*Primary Examiner* — Ryan M Gray
(74) *Attorney, Agent, or Firm* — Thorpe North & Western, LLP.

(57) ABSTRACT

Augmenting real-time views of a patient with three-dimensional (3D) data. In one embodiment, a method may include identifying 3D data for a patient with the 3D data including an outer layer and multiple inner layers, determining virtual morphometric measurements of the outer layer from the 3D data, registering a real-time position of the outer layer of the patient in a 3D space, determining real-time morphometric measurements of the outer layer of the patient, automatically registering the position of the outer layer from the 3D data to align with the registered real-time position of the outer layer of the patient in the 3D space using the virtual morphometric measurements and using the real-time morphometric measurements, and displaying, in an augmented reality (AR) headset, one of the inner layers from the 3D data projected onto real-time views of the outer layer of the patient.

22 Claims, 11 Drawing Sheets

Related U.S. Application Data continuation of application No. 16/574,524, filed on Sep. 18, 2019, now Pat. No. 11,004,271, which is a continuation of application No. 15/894,595, filed on Feb. 12, 2018, now Pat. No. 10,475,244, which is a continuation of application No. 15/474,702, filed on Mar. 30, 2017, now Pat. No. 9,892,564.

(51) Int. Cl.

| | | |
|---|---|---|
| *A61B 5/107* | (2006.01) | |
| *A61B 7/00* | (2006.01) | |
| *G06T 7/246* | (2017.01) | |
| *G06T 7/73* | (2017.01) | |
| *G06T 15/04* | (2011.01) | |
| *G06T 19/20* | (2011.01) | |
| *G16H 20/40* | (2018.01) | |
| *G16H 30/40* | (2018.01) | |
| *G16H 40/63* | (2018.01) | |
| *H04N 7/14* | (2006.01) | |

(52) U.S. Cl.
CPC ............ *A61B 5/0077* (2013.01); *A61B 5/107* (2013.01); *A61B 5/742* (2013.01); *A61B 7/00* (2013.01); *G06T 7/248* (2017.01); *G06T 7/73* (2017.01); *G06T 15/04* (2013.01); *G06T 19/20* (2013.01); *G16H 20/40* (2018.01); *G16H 30/40* (2018.01); *G16H 40/63* (2018.01); *H04N 7/147* (2013.01); *A61B 2562/0219* (2013.01); *A61B 2562/0223* (2013.01); *G06T 2200/04* (2013.01); *G06T 2207/10016* (2013.01); *G06T 2207/10024* (2013.01); *G06T 2207/30024* (2013.01); *G06T 2207/30088* (2013.01); *G06T 2207/30204* (2013.01); *G06T 2210/41* (2013.01); *G06T 2215/16* (2013.01); *G06T 2219/2004* (2013.01); *G06T 2219/2012* (2013.01)

(56) References Cited

U.S. PATENT DOCUMENTS

| | | | | |
|---|---|---|---|---|
| 10,052,170 | B2* | 8/2018 | Saget | G06T 11/60 |
| 11,004,271 | B2* | 5/2021 | Cvetko | G16H 20/40 |
| 11,481,987 | B2* | 10/2022 | Cvetko | A61B 5/0015 |
| 2004/0254456 | A1 | 12/2004 | Ritter | |
| 2005/0203367 | A1 | 9/2005 | Ahmed | |
| 2005/0289472 | A1 | 12/2005 | Morita | |
| 2013/0177229 | A1* | 7/2013 | Inoue | A61B 8/5223 382/131 |
| 2013/0245461 | A1* | 9/2013 | Maier-Hein | A61B 90/361 600/476 |
| 2014/0132605 | A1* | 5/2014 | Tsukagoshi | A61B 6/466 345/424 |
| 2015/0178885 | A1* | 6/2015 | Kwon | A61B 6/461 345/646 |
| 2016/0078669 | A1 | 3/2016 | Lin | |
| 2017/0172696 | A1* | 6/2017 | Saget | A61B 90/37 |
| 2018/0020992 | A1* | 1/2018 | Guo | A61B 8/483 600/424 |
| 2018/0303558 | A1* | 10/2018 | Thomas | A61B 34/20 |

* cited by examiner

AUGMENTING REAL-TIME VIEWS OF A PATIENT WITH THREE-DIMENSIONAL DATA

CROSS-REFERENCE TO A RELATED APPLICATION

This application is a continuation of U.S. patent application Ser. No. 17/316,222, filed May 10, 2021, now U.S. Pat. No. 11,481,987, which is a continuation of U.S. patent application Ser. No. 16/574,524, filed Sep. 18, 2019, now U.S. Pat. No. 11,004,271, which is a continuation of U.S. patent application Ser. No. 15/894,595, filed Feb. 12, 2018, now U.S. Pat. No. 10,475,244, which is a continuation of U.S. patent application Ser. No. 15/474,702, filed Mar. 30, 2017, now U.S. Pat. No. 9,892,564, each of which is incorporated herein by reference in its entirety for all that it discloses.

BACKGROUND

Augmented reality (AR) systems generally take a user's live view of a real-world environment and augment that view with computer-generated virtual elements such as video, sound, or graphics. As a result, AR systems function to enhance a user's current perception of reality.

One common problem faced by AR systems is accurately aligning the position of a virtual element with a live view of a real-world environment. This alignment process is often done manually or is done automatically only after manual placement of non-anatomical fiducials. In either case, the manual process can be time consuming, cumbersome, and inaccurate.

Another common problem faced by AR systems is proper placement of virtual controls for managing virtual elements. Virtual controls, while intended to aide a user in interacting with virtual elements, are often placed in positions in the live view that render them more of a hindrance than a help to the user.

The subject matter claimed herein is not limited to embodiments that solve any disadvantages or that operate only in environments such as those described above. Rather, this background is only provided to illustrate one example technology area where some embodiments described herein may be practiced.

SUMMARY

In one embodiment, a method for augmenting real-time views of a patient with three-dimensional (3D) data may include various acts. For example, the method may include identifying 3D data for a patient with the 3D data including an outer layer of the patient and multiple inner layers of the patient. The method may also include determining virtual morphometric measurements of the outer layer of the patient from the 3D data. The method may further include registering a real-time position of the outer layer of the patient in a 3D space. The method may also include determining real-time morphometric measurements of the outer layer of the patient. The method may further include automatically registering the position of the outer layer of the patient from the 3D data to align with the registered real-time position of the outer layer of the patient in the 3D space using the virtual morphometric measurements and using the real-time morphometric measurements. The method may also include displaying, in an augmented reality headset, one of the inner layers of the patient from the 3D data projected onto real-time views of the outer layer of the patient.

In another embodiment, a method for augmenting real-time views of a patient with 3D data may include various acts. For example, the method may include identifying 3D data for a patient with the 3D data including an outer layer of the patient and multiple inner layers of the patient. The method may also include displaying, in an augmented reality headset, one of the inner layers of the patient from the 3D data projected onto real-time views of the outer layer of the patient. The method may further include generating, in the augmented reality headset, a virtual user interface that includes options for altering the display of the projected inner layer of the patient from the 3D data. The method may also include displaying, in the augmented reality headset, the virtual user interface projected onto real-time views due to a focal orientation of the augmented reality headset not being focused on the patient. The method may further include hiding, in the augmented reality headset, the virtual user interface due to the focal orientation of the augmented reality headset being focused on the patient.

It is to be understood that both the foregoing summary and the following detailed description are explanatory and are not restrictive of the invention as claimed.

BRIEF DESCRIPTION OF THE DRAWINGS

Embodiments will be described and explained with additional specificity and detail through the use of the accompanying drawings in which.

DETAILED DESCRIPTION

Figure 1:
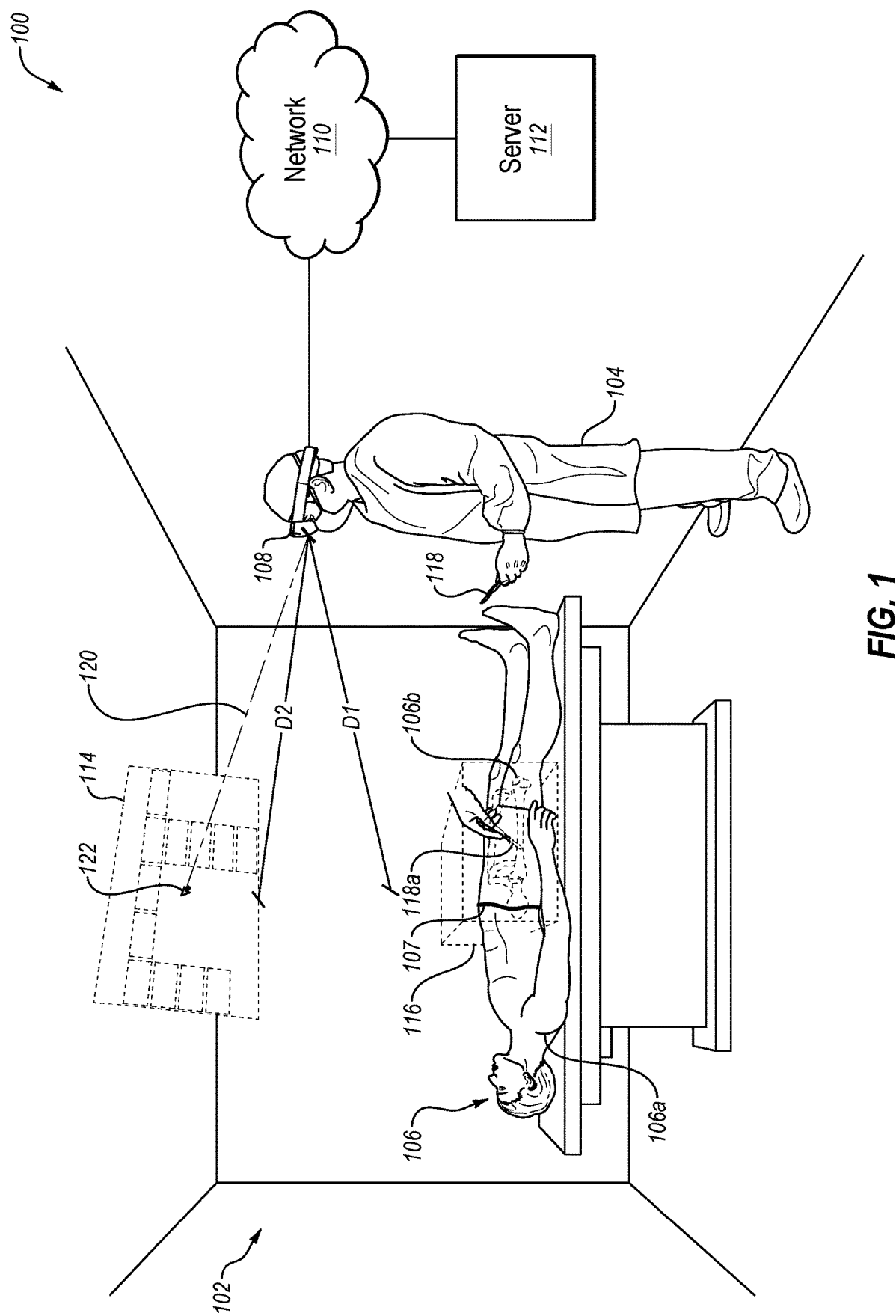
FIG. 1 illustrates an example augmented reality (AR) environment in which real-time views of a patient may be augmented with three-dimensional (3D) data.
Figure 2A:
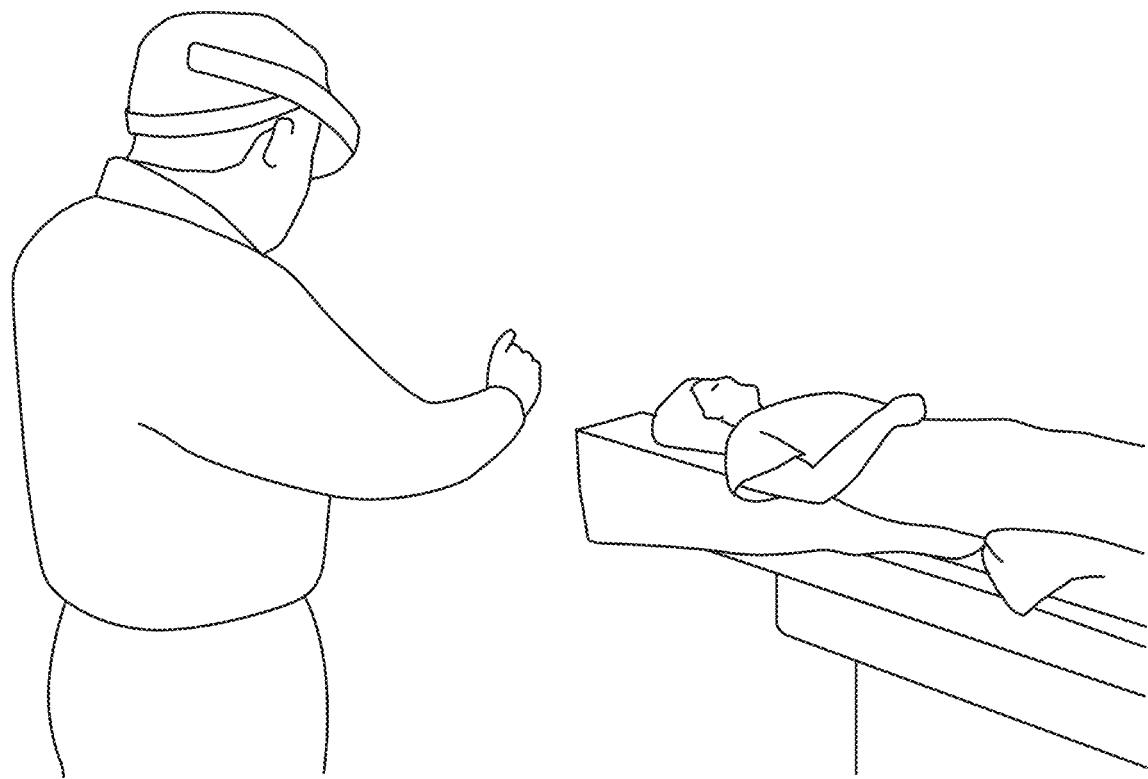
FIGS. 2A-2F are photographs of the AR environment of FIG. 1 with a first patient.
Figure 2B:
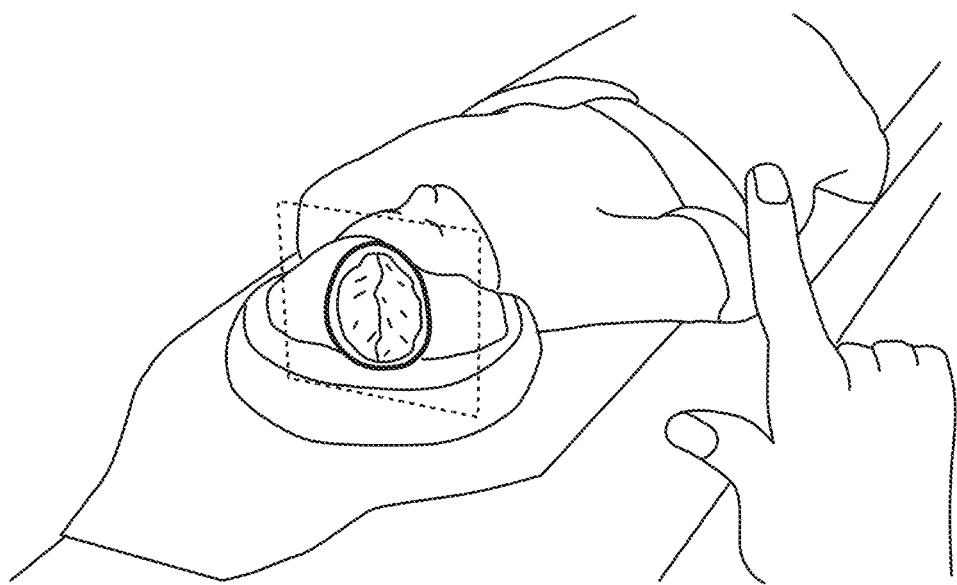
Figure 2C:
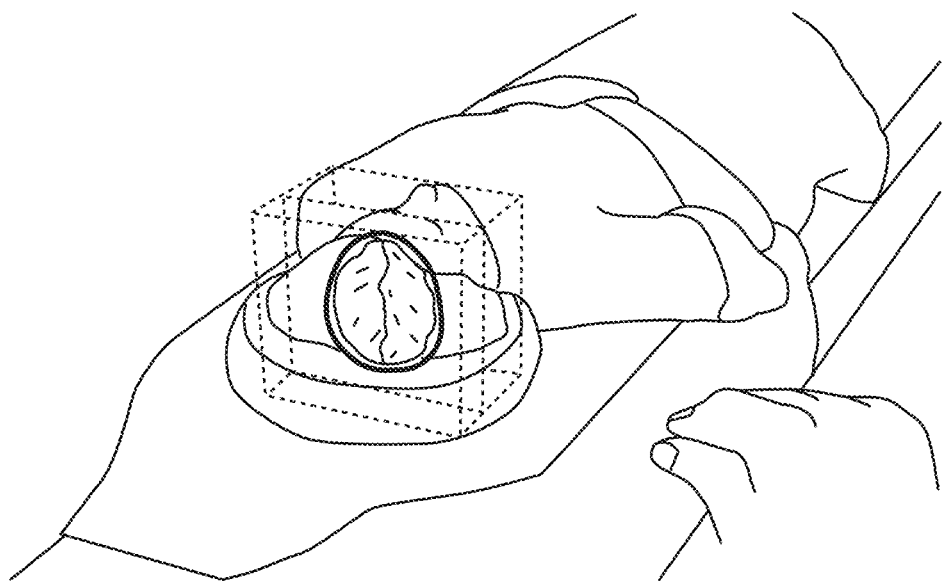
Figure 2D:
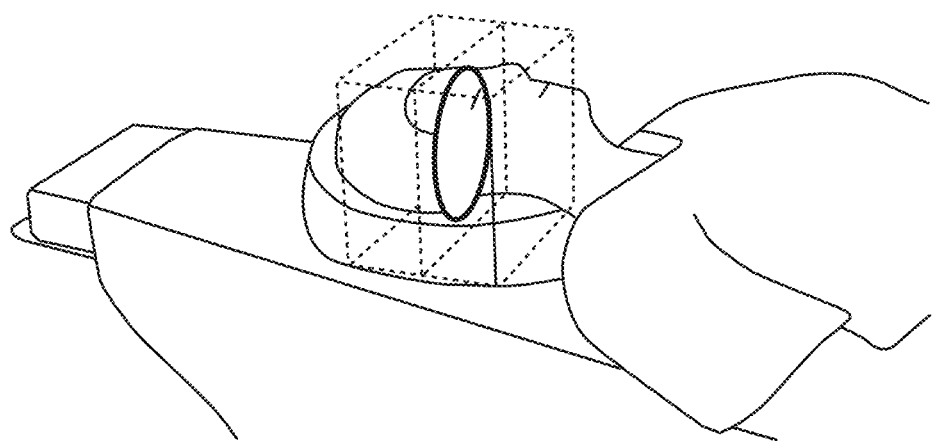
Figure 2E:
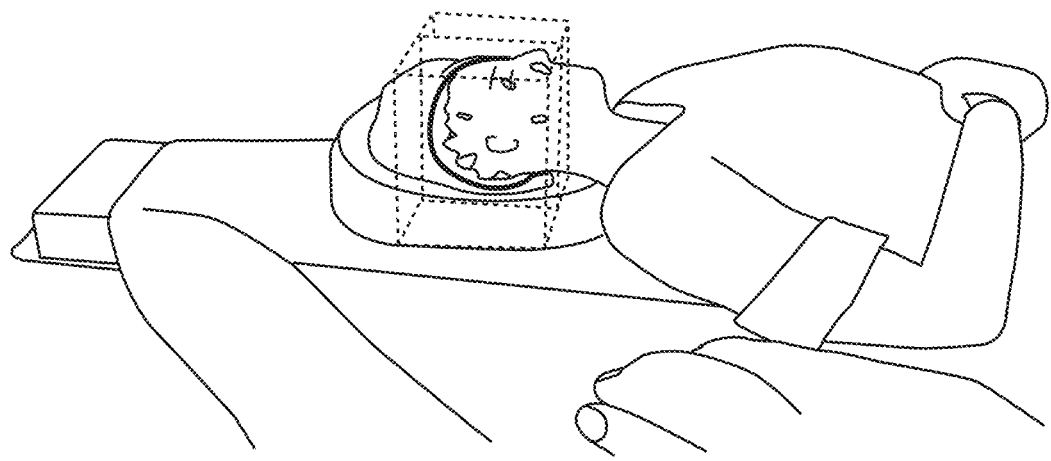
Figure 2F:
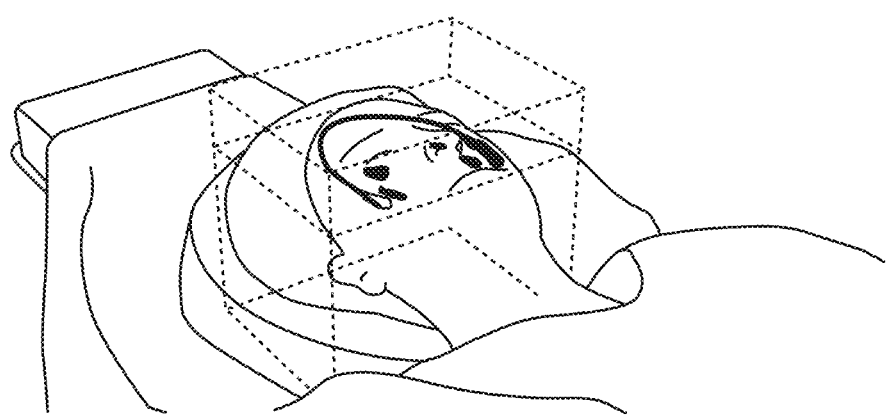

Medical imaging may be employed to create visual representations of the interior of a patient. More particularly, medical imaging may be employed to reveal internal structures hidden by an outer layer of a patient, such as the skin, for various purposes such as training, research, diagnosis, and treatment.

Conventional medical imaging systems may create three-dimensional (3D) data for a patient and then display that 3D data as an image or images on a computer display. While viewing images of a patient on a computer display, detached from the actual patient, may be useful in training, research, diagnosis, and treatment, viewing, such detached viewing may also result in some problems.

For example, where a surgeon needs to remove a tumor from a patient's brain, the surgeon may view an image of the patient's brain on a computer display. After viewing the location of the tumor on the computer display, the surgeon may then shift his view from the computer display to the actual patient on an operating table and attempt to identify the approximate location on the actual patient of the tumor inside the patient's brain. This method of identifying the approximate location of the tumor can be difficult and error-prone. For example, the surgeon may accidentally identify the left side of the brain in the image as having the tumor when in reality the tumor is in the right side of the brain. This error may lead to the surgeon erroneously making an unnecessary incision on the left side of the patient's skull.

In another example, where a doctor needs to perform knee surgery on a patient, the doctor may view an image of the patient's knee on a computer display. After viewing the problematic area of the knee on the computer display, the doctor may then shift his view from the computer display to the actual patient on an operating table and attempt to identify the problematic area of the knee on the actual patient for the surgery. This method of identifying the problematic area of the knee can be difficult and error-prone. For example, the doctor may accidentally pull up images of the wrong patient on the computer display, without realizing that the patient on the operating table does not match the images on the computer display. This error may lead to the surgeon erroneously making an incision in the wrong location due to natural variation of problematic areas of the knee from one patient to the next.

The embodiments disclosed herein may provide various benefits over a conventional medical imaging system. In particular, the embodiments disclosed herein may, for example, augment real-time views of a patient with 3D data. In some embodiments, the 3D data of a patient may be automatically aligned, or registered, with a real-time view of the actual patient and then images derived from the 3D data may be projected onto the real-time view of the patient. Thus, these embodiments may enable a medical professional to view a virtual interior of the patient while looking at the actual patient without any time consuming, cumbersome, and inaccurate manual alignment and/or without any time consuming, cumbersome, and inaccurate manual placement of non-anatomical fiducial. When used in training, research, diagnosis, or treatment, these embodiments may enable a medical professional to more easily and more accurately locate a target location within a patient.

For example, when employed in the brain surgery example discussed above, these embodiments may avoid the surgeon getting confused on the location of the tumor between the right and left sides of the brain, and may thereby avoid the surgeon making an unnecessary incision on the wrong side of the skull during the surgery to remove the tumor. Similarly, when employed in the knee surgery example discussed above, these embodiments may avoid the doctor using 3D data for the wrong patient because the automatic alignment may fail or may indicate a low confidence that the automatic alignment was correct, thus alerting the doctor that the patient data may not be for the patient currently on the operating table.

Further, in some embodiments, the augmenting of real-time views of a patient with 3D data may include the display of a virtual user interface and other virtual controls for altering the images projected onto the real-time view of the patient. This virtual user interface and these other virtual controls may be projected to avoid obstructing the medical professional's field of view when viewing the patient, to maintain a relatively constant focal length for the medical professional, and/or to maintain the orientation of the virtual user interface facing the medical professional. In this way, these embodiments may allow the medical professional to quickly and easily alter the images projected onto the real-time view of the patient.

Turning to the figures, FIG. 1 illustrates an example augmented reality (AR) environment 100. In some embodiments, the environment 100 may include a 3D space 102, a user 104, a patient 106, and an AR headset 108 which may be in communication with a server 112 over a network 110. In some embodiments, the environment 100 may also include a virtual user interface 114, a virtual spatial difference box 116, a virtual inserted portion 118a of an object 118, and a virtual cursor 122, all shown in dashed lines to indicate that these virtual elements are generated by the AR headset 108 and only viewable by the user 104 through the AR headset 108.

In some embodiments, the 3D space 102 may be any 3D space including, but not limited to, an operating room with an operating table 103 (as illustrated in FIG. 1), an office, a classroom, or a laboratory. In some embodiments, the 3D space 102 may be a space where the user 104 may view the patient 106 while wearing the AR headset 108.

In some embodiments, the user 104 may be any user of the AR headset 108 including, but not limited to, a medical professional (as illustrated in FIG. 1), an instructor, a researcher, a patient, or a caregiver of a patient. For example, a medical professional may use the AR headset 108 in order to perform a medical procedure on the patient 106. Similarly, a researcher or an instructor may use the AR headset 108 while performing medical research or instructing medical students. Further, a caregiver of the patient 106, or the patient 106 himself, may use the AR headset 108 when a medical professional is attempting to explain a suggested medical procedure for the patient 106.

In some embodiments, the patient 106 may be any animal, either conscious or unconscious, either living or dead, either whole or missing one or more body parts. For example, the patient 106 may be a living human adult (as illustrated in FIG. 1) who has been rendered unconscious in order to undergo a medical procedure by the user 104. In another example, the patient 106 may be a cadaver of a human adult that will undergo a dissection for research or training purposes. In another example, the patient 106 may be a conscious animal that is being evaluated by a veterinarian in order to diagnose a medical condition. In another example, the patient 106 may be a single limb or organ of a deceased human.

In some embodiments, the AR headset 108 may be any computer system in the form of an AR headset that is capable of augmenting real-time views of the patient 106 with 3D data. For example, the AR headset 108 may be employed by the user 104 in order to augment a realtime view of the patient 106 with one or more inner layers of the patient 106 including, but not limited to, bones 106b (as illustrated in FIG. 1), muscles, organs, or fluids. In some embodiments, the AR headset 108 may perform this augmenting of a real-time view of the patient 106 regardless of the current position of the user 104 in the 3D space 102. For example, the user 104 may walk around the operating table 103 and view the patient 106 from any angle within the 3D space 102, and all the while the AR headset 108 may continually augment the real-time view of the patient 106 with one or more inner layers of the patient 106, so that both the patient 106 and the 3D data of the patient 106 may be viewed by the user 104 from any angle within the 3D space 102. The AR headset 108 may perform this augmenting of a real-time view of the patient 106 with 3D data according to the method 600 disclosed herein in connection with FIGS. 6A-6E. In some embodiments, the AR headset 108 may be a modified version of the Microsoft HoloLens.

In some embodiments, the network 110 may be configured to communicatively couple the AR headset 108 and the server 112 or other computer system(s). In some embodiments, the network 110 may be any wired or wireless network, or combination of multiple networks, configured to send and receive communications between systems and devices. In some embodiments, the network 110 may include a Personal Area Network (PAN) such as a Bluetooth network, a Local Area Network (LAN) such as a WiFi network, a Metropolitan Area Network (MAN), a Wide Area Network (WAN), or a Storage Area Network (SAN). In some embodiments, the network 110 may also be coupled to, or may include, portions of a telecommunications network for sending data in a variety of different communication protocols, such as a cellular network.

In some embodiments, the server 112 may be any computer system capable of functioning in connection with the AR headset 108. In some embodiments, the server 112 may be configured to communicate in real-time with the AR headset 108 in order to convey 3D data to, or receive data from, the AR headset 108. In addition, the server 112 may be employed to offload some or all of the data storage or processing desired by the AR headset 108.

In some embodiments, the virtual user interface 114 may be any virtual user interface generated by the AR headset 108 that includes options for altering the display of the projected inner layer(s) of the patient 106 from the 3D data of the patient 106. For example, the options included in the virtual user interface 114 may include, but are not limited to, options that cause the AR headset 108 to:

(1) quit viewing the augmented view of the patient 106,
(2) display a demo of the capabilities of the AR headset 108,
(3) adjust the characteristics of the 3D data that is projected onto the patient 106, such as the brightness and color of the projected 3D data,
(4) adjust the alignment of the 3D data with the patient 106,
(5) display the virtual spatial difference box 116,
(6) display a slice of the 3D data instead of a volume of the 3D data,
(7) drag the 3D data in a direction of the user 104, such as in the repositioning of a slice of the 3D data,
(8) display different slices of the 3D data including, but not limited to, axial slices, coronal slices, sagittal slices, and oblique slices, and
(9) perform other advanced features of the AR headset 108.

The virtual user interface 114 may further include other information that may be useful to the user 104. For example, the virtual user interface 114 may include real-time vital signs for the patient 106 such as heart-rate, blood-pressure, and respiration-rate. In another example, the virtual user interface 114 may include a stopwatch showing the amount of time the patient 106 has been unconscious.

In some embodiments, the AR headset 108 may be configured to display the virtual user interface 114 at a comfortable distance from the user 104 and/or in a comfortable orientation for the user 104. For example, the AR headset 108 may be configured to display the virtual user interface 114 at a focal distance D2 from the AR headset 108 that is about equal to a real-time distance D1 of the patient 106 from the AR headset 108. This distance may be comfortable for the user because it may avoid the user 104 from having to refocus his eyes when shifting his focus between the patient 106 and the virtual user interface 114, even as the user moves around the 3D space 102 and even as the user moves closer to and further away from the patient 106. In another example, the AR headset 108 may be configured to display the virtual user interface 114 at a focal orientation that is oriented perpendicularly to a focal orientation 120 of the AR headset 108. This orientation may be comfortable for the user 104 because it may cause the virtual user interface 114 to constantly face the user 104 head-on regardless of the current focal orientation 120 of the AR headset 108, even as the user moves around the 3D space 102 and even as the user generally faces toward or faces away from the patient 106.

In some embodiments, the virtual spatial difference box 116 may be generated by the AR headset 108 to confine within a volume of the virtual spatial difference box 116 the projected inner layer of the patient 106 from the 3D data. For example, the projected bones 106b of the patient 106 may be confined within the virtual spatial difference box 116 in FIG. 1. In some embodiments, the virtual spatial difference box 116 may also assist the user when navigating the projected 3D data by providing a frame of reference for the user 104. For example, this frame of reference may assist the user when moving axial slices, coronal slices, sagittal slices, or oblique slices of the 3D data within the virtual spatial difference box 116. Slices may be two-dimensional (2D) slices and/or 3D slices. 3D slices may include curved slices, such as curved slices that follow the natural curve of an anatomical feature, or slices that have a depth as well as a height and width. The user 104 may move these slices using hand gestures that require the user 104 to generally move his hand in the directions of the lines of the virtual spatial difference box 116, so the display of the virtual spatial difference box 116 may make these hand movements easier for the user 104.

In some embodiments, the virtual inserted portion 118a of the object 118 may correspond to any portion of the object 118 that the user 104 wishes to insert into the patient 106 though an outer layer of the patient 106. For example, the object 118 may include, but is not limited to, a scalpel (as illustrated in FIG. 1), a scope, a drill, a probe, another medical instrument, or even the hand of the user 104. Similar to the registration of the real-time position of the outer layer of the patient 106, the position of the outer layer of the object 118 may also be registered. However, unlike the patient 106, which may remain relatively still in the environment 100, the object 118 may be frequently moved in the environment 100, such that the real-time position of the object 118 may be automatically tracked in the 3D space 102 with respect to the registered positions of the outer layer of the patient 106. Then, in the event that the user 104 inserts some portion of the object 118 into the outer layer of the patient 106, the AR headset 108 may display a virtual inserted portion 118a of the object 118 projected into the projected inner layer of the patient 106 from the 3D data. In this manner, the virtual inserted portion 118a of the object 118 may be projected onto the real-time view of the user 104 even when the actual inserted portion of the object 118 is hidden from the real-time view of the user 104.

In some embodiments, the object 118 may be specifically designed to enable more accurate tracking of the object 118 by the AR headset 108. For example, where the object 118 is a relatively small medical instrument, such as a syringe with a needle, the object 118 may be enhanced to be more easily sensed by sensors of the AR headset 108. For example, these medical instruments may be sized larger to be more easily sensed (by a visual sensor for example), may be given a specific shape to be more easily sensed (such as by shaping the tip of the syringe to which the needle attaches as a sphere), may be made more visible to be more easily sensed (such as by adding a reflective strip or a light strip), or may be made from a material that is more easily sensed (such as by being made from metal to be more easily sensed by a metal detector sensor).

Further, in some embodiments, an attachment may be added to the object 118, such as to a handle of the object 118, to enable more accurate tracking of the object 118 by the AR headset 108. For example, the attachment may include any of the enhancements noted above to make the attachment more easily sensed by sensors of the AR headset 108 and, by virtue of the attachment being attached to the object 118, thereby also making the object 118 more easily sensed by sensors of the AR headset 108. Further, the attachment may be designed to attach to the portion of the object 118 that is intended to be inserted into the patient 106, such as the tip of the object 118, so that sensors of the AR headset 108 can actually sense the attachment inside the patient 106. For example, a small magnetic-field-emitting attachment may be attached to a tip of the object 118, and a magnetic sensor of the AR headset I 08 may then be able to sense the exact location of the attachment within the patient I 06, thereby helping to improve the accuracy of the virtual inserted portion 118a displayed to the user 104.

In some embodiments, the virtual cursor 122 may be a virtual cursor generated by the AR headset 108 on the virtual user interface 114, on another virtual control, or at any other position in the 3D space 102. In some embodiments, the position of the virtual cursor 122 may correspond to the focal orientation 120 of the AR headset 108, which may correspond to the orientation of the head of the user 104. The virtual cursor 122 may be employed by the user 104 to select one or more options of the virtual user interface 114, sometimes in connection with one or more other actions by the user 104, such as a blink of the user's eyes, or one or more hand gestures of the user 104, such as the tapping together of two fingers in the field of view of the AR headset 108.

Modifications, additions, or omissions may be made to the environment 100 without departing from the scope of the present disclosure. For example, in some embodiments, multiple users each wearing an AR headset 108 may be simultaneously present in the 3D space 102 in order to simultaneously view the patient 106 augmented with 3D data of the patient 106. In another example, multiple patients may be simultaneously present in the 3D space 102 in order to allow the user 104 wearing the AR headset 108 to simultaneously view the multiple patients augmented with 3D data of the patients. In another example, multiple users each wearing an AR headset 108 and multiple patients may simultaneously be present in the 3D space. In another example, video of the view from the AR headset 108 may be captured by the AR headset 108 and then sent to a remote location, such as to the server 112 over the network 110 or to a remote AR headset or Virtual Reality (VR) headset for viewing by another user. This example may enable the remote user to guide the local user 104 through a medical procedure on the patient 106. Further, although the environment 100 is generally disclosed to be in the context of a user 104 viewing a patient 106, it is understood that the environment 100 may be more broadly defined as any environment where a user wishes to view one or more inner layers of any object, such as a tree, a rock, an oilfield, or a planet.

In another example, the AR headset 108 may additionally or alternatively be controlled by the user 104 using voice commands. For example, the user 104 may employ voice commands because his hands are occupied with surgery or other medical treatment on the patient 106, and therefore controlling the AR headset 108 headset using hand gestures is not convenient. In this example, the voice commands may be employed to control the virtual user interface 114 (e.g., to select an option on the virtual user interface 114), the virtual spatial difference box 116 (e.g., to toggle between displaying and hiding the virtual spatial difference box 116 or to reposition slices of 3D data displayed in the virtual spatial difference box 116), or the virtual cursor 122 (e.g., to toggle between displaying and hiding the virtual cursor 122 projected onto the patient 106), or some combination thereof. Further, in this example, the voice commands may be employed separately from any other virtual controls. For example, voice commands may be employed to toggle between displaying and hiding, or to adjust the level of transparency of, the 3D data projected onto the patient 106, which may be useful while the user 104 is performing surgery on the patient 106 and may allow the user 104 to only view the projected 3D data when it is needed and to avoid viewing the projected 3D data, or make the 3D data more transparent, when the 3D data becomes a distraction. In another example, controls of the AR headset 108, such as the virtual user interface 114, may present options to the user 104, at least in part, audibly. The audible presentation of options may allow the user 104 to first hear voice options (e.g., potential voice commands) before actually speaking voice commands. The audible presentation of options may also allow the user 104 to maintain the focal orientation 120 of the AR headset 108, and/or the visual focus of the user 104, on the patient 106 while still being able to interact with a virtual control that is not currently in his field of vision and/or that is currently hidden by the AR headset 108.

FIGS. 2A-2F are photographs of the AR environment 100 of FIG. 1 with a first patient. As disclosed in FIG. 2A, a user may wear an AR headset that augments a real-time view of the first patient with 3D data of the first patient. Also disclosed in FIG. 2A, the user may employ hand gestures in order to manipulate virtual controls of the AR headset. FIGS. 2B-2F disclose actual views from the perspective of the user wearing an AR headset. As disclosed in FIG. 2B, a user may employ a hand gesture in order to have an axial slice of 3D data representing a CT image of the patient's brain projected onto a real-time view of the first patient. As disclosed in FIG. 2C, a virtual spatial difference box may be employed by the user to view the same axial slice of the 3D data representing the CT image of the first patient's brain. As disclosed in FIG. 2D, as the user wearing the AR headset walks counter-clockwise around the first patient, the same axial slice of the 3D data representing the CT image of the first patient's brain may be viewed from different angles in the 3D space. As disclosed in FIGS. 2E and 2F, the user may manipulate one or more options of a virtual user interface to change from viewing the axial slice to a sagittal slice, and then from the sagittal slice to a coronal slice, respectively.

Figure 3:
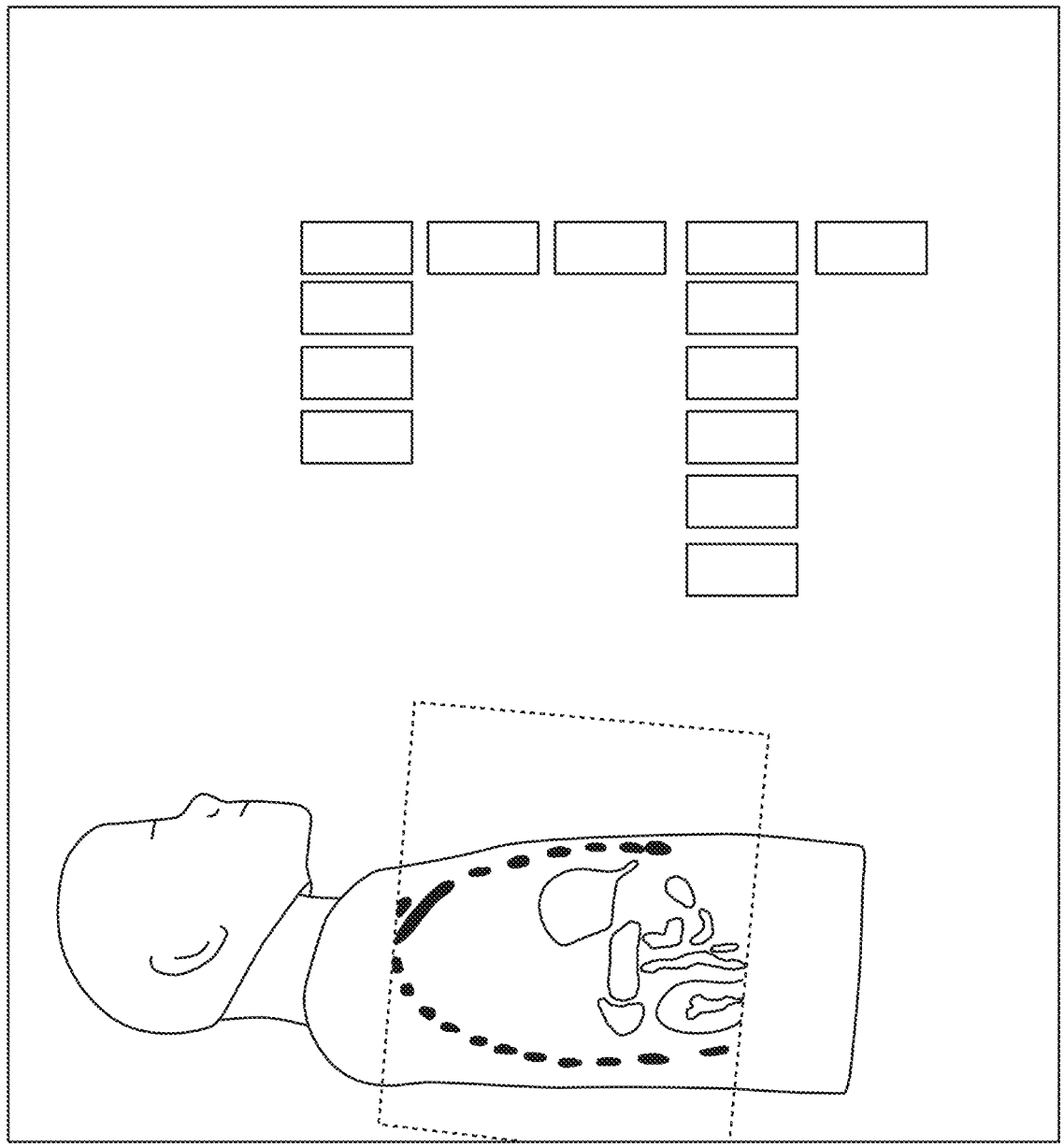
FIG. 3 is a photograph of the AR environment of FIG. 1 with a second patient.

FIG. 3 is a photograph of the AR environment of FIG. 1 in use with a second patient. In particular, FIG. 3 discloses an actual view from the perspective of the user wearing an AR headset. As disclosed in FIG. 3, the AR headset may update, in real-time, the displaying of a virtual user interface to cause the virtual user interface to be continually positioned at a focal distance from the AR headset that is about equal to the real-time distance of the second patient from the AR headset. Further, the AR headset may update, in real-time, the displaying of the virtual user interface to cause the virtual user interface to continually be oriented perpendicularly to the focal orientation of the AR headset.

Figure 4A:
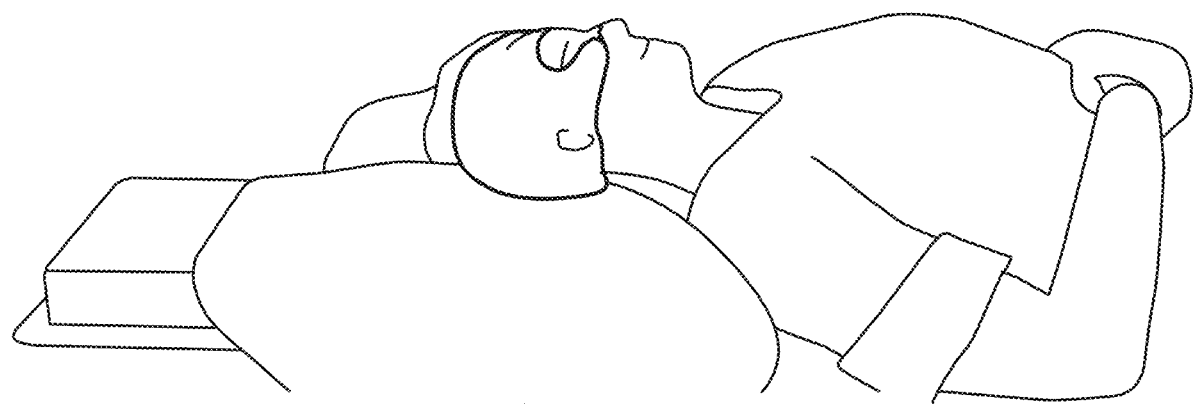
FIGS. 4A-4B are photographs of the AR environment of FIG. 1 with a third patient.
Figure 4B:
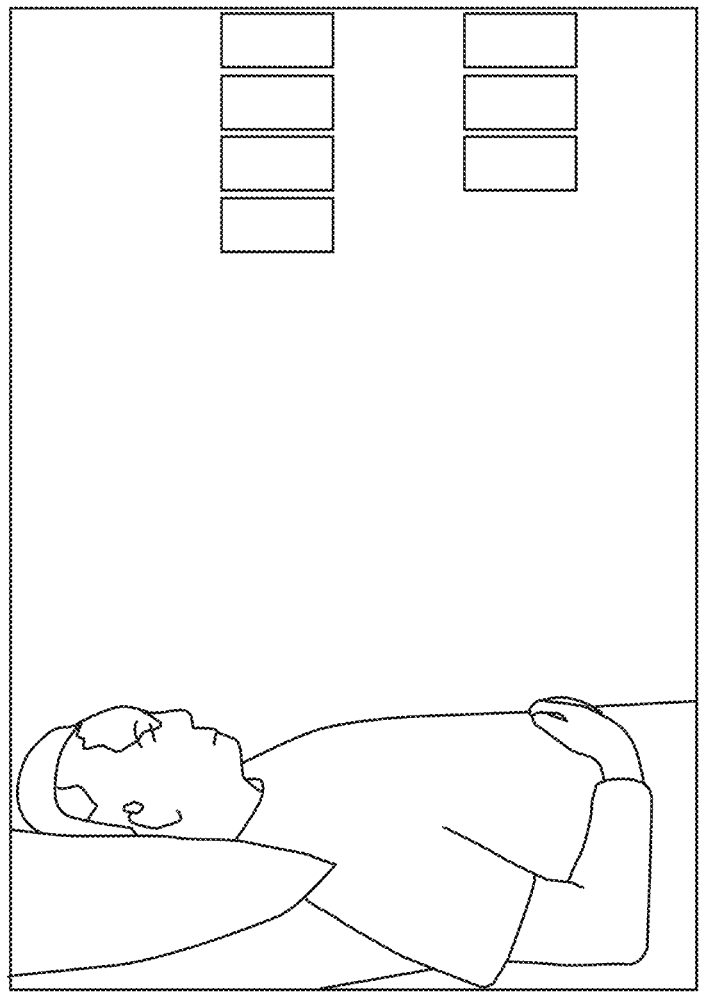

FIGS. 4A-4B are photographs of the AR environment of FIG. 1 with a third patient. In particular, FIGS. 4A-4B disclose an actual view from the perspective of the user wearing an AR headset. As disclosed in a comparison of FIGS. 4A and 4B, the AR headset may be configured to display the virtual user interface projected onto a real-time view (as disclosed in FIG. 4B) while a focal orientation of the AR headset is not focused on the third patient, but then hide the virtual user interface while the focal orientation of the AR headset is focused on the third patient. In this manner, the AR headset may avoid the virtual user interface from obstructing the view of the third patient. In some embodiments, and since the third patient is generally positioned below a horizontal view, the AR headset may avoid the virtual user interface from obstructing the view of the third patient by displaying the virtual user interface when the focal orientation of the AR headset is above horizontal and by hiding the virtual user interface when the focal orientation of the AR headset is at or below horizontal. In these embodiments, the user can view the virtual user interface by simply looking up at any time while wearing the AR headset.

As disclosed in the photographs of FIGS. 2A-4B, the projected inner layers of the 3D data of the three patients may be colored using color gradients that represent tissue properties and that are altered, from standard color gradients, to be visible when projected onto the real-time views of the outer layer of the three patients. For example, in some embodiments where the 3D data includes one or more of CT scan images and X-ray images, the tissue properties represented by the color gradient may include tissue hardness ranging from softest tissue to hardest tissue. In other embodiment, the tissue properties represented by the color gradient may include, but are not limited to, one or more of relaxivity, echogenicity, enhancement amount, enhancement speed, density, radioactivity, and water content. In order for the color gradient to be easily visible by the user wearing the AR headset, the color gradient may be altered to be lighter in color than standard color gradients used on computer displays since darker color gradients may blend into the view of the patient when projected onto the patient.

Figure 5:
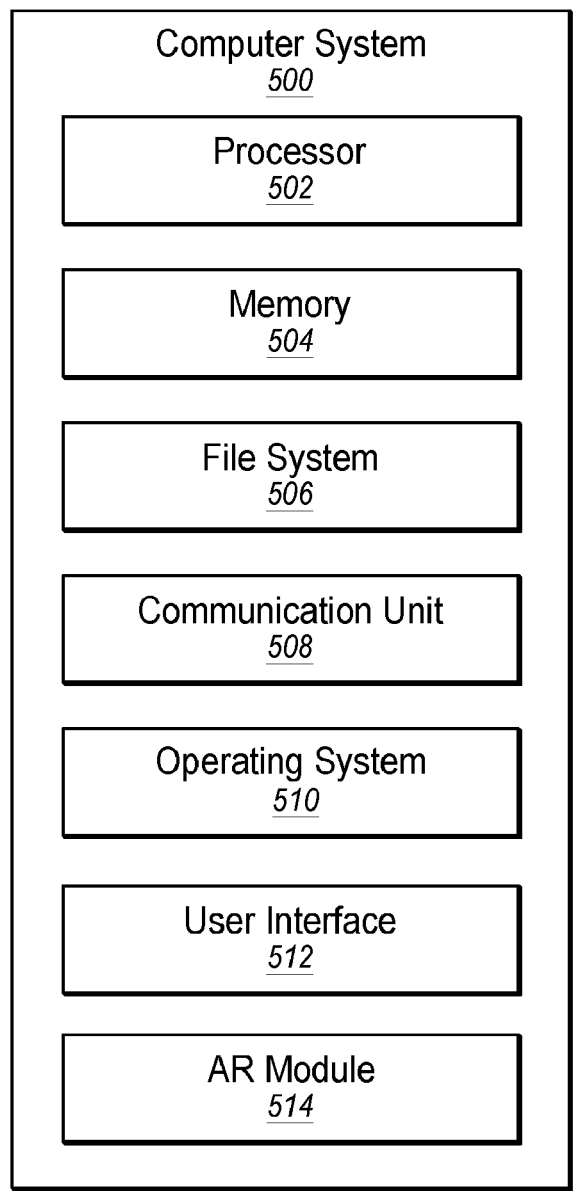
FIG. 5 illustrates an example computer system that may be employed in augmenting real-time views of a patient with 3D data.
Figure 6A:
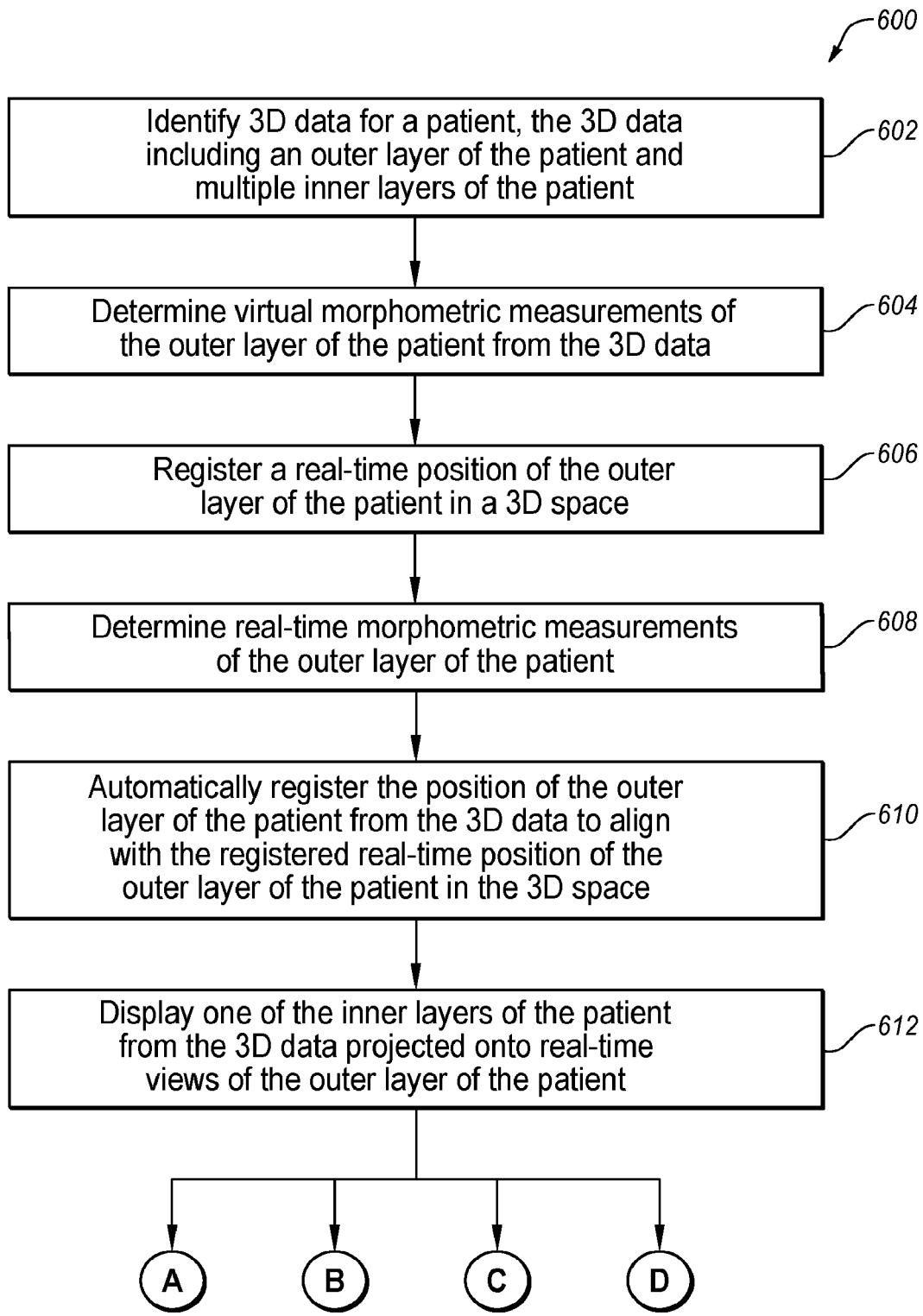
FIGS. 6A-6E are a flowchart of an example method of augmenting real-time views of a patient with 3D data.
Figure 6B:
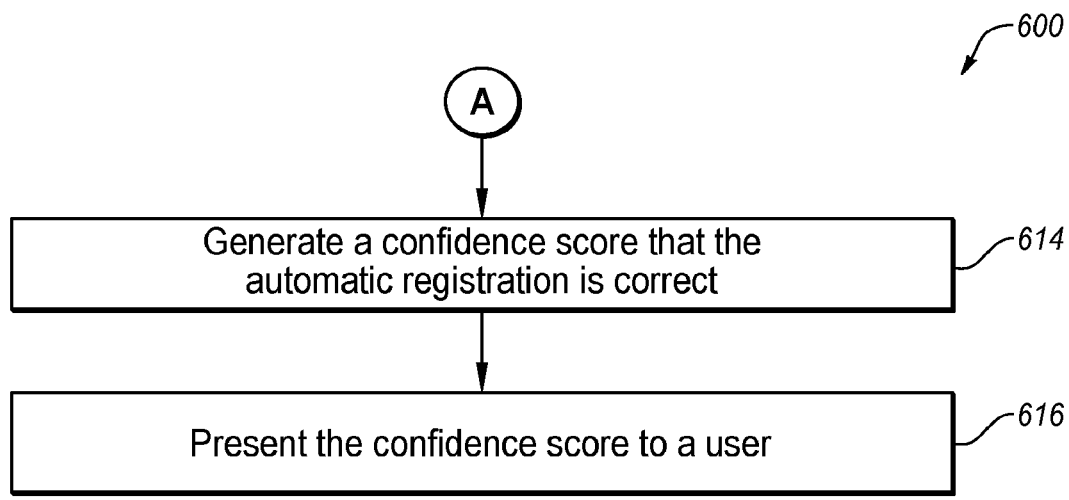
Figure 6C:
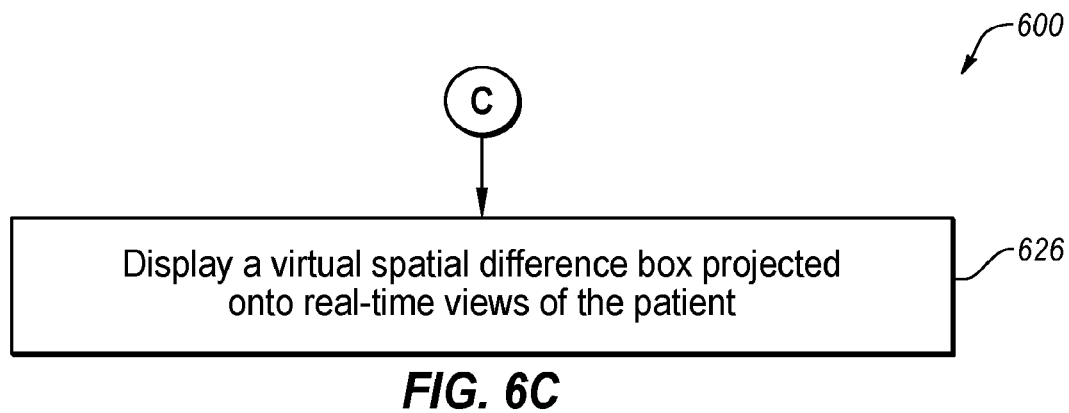
Figure 6D:
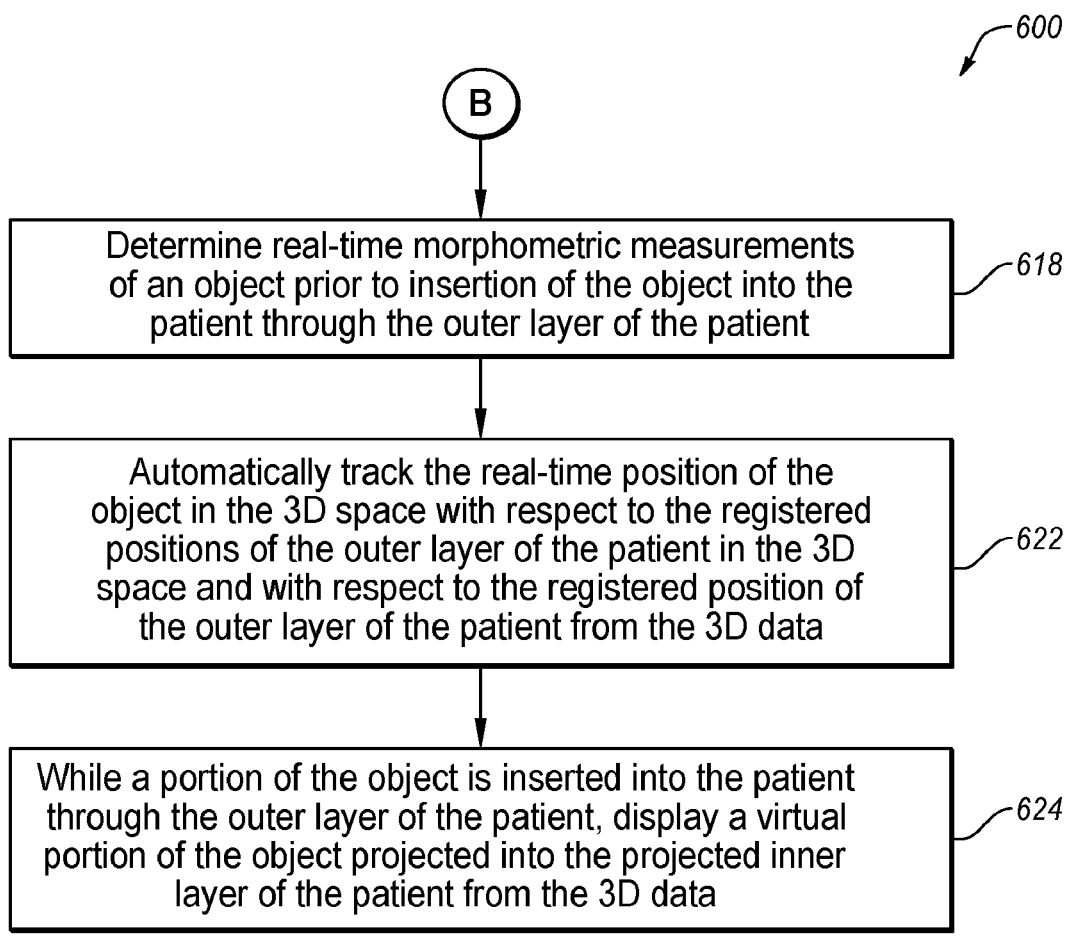
Figure 6E:
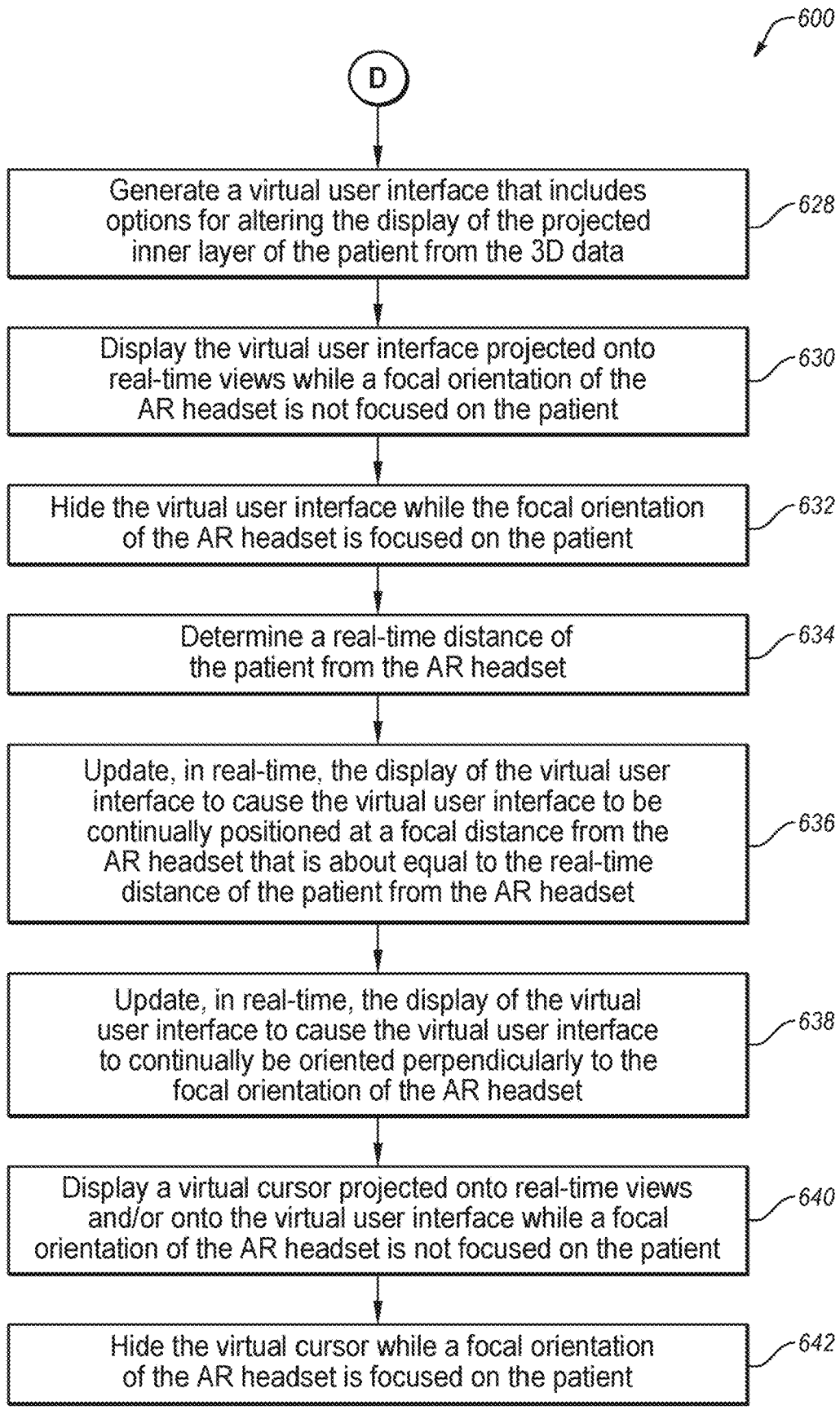

FIG. 5 illustrates an example computer system 500 that may be employed in augmenting views of a patient with 3D data. In some embodiments, the computer system 500 may be part of any of the systems or devices described in this disclosure. For example, the computer system 500 may be part of any of the AR headset 108 or the server 112 of FIG. 1.

The computer system 500 may include a processor 502, a memory 504, a file system 506, a communication unit 508, an operating system 510, a user interface 512, and an AR module 514, which all may be communicatively coupled. In some embodiments, the computer system 500 may be, for example, a desktop computer, a client computer, a server computer, a mobile phone, a laptop computer, a smartphone, a smartwatch, a tablet computer, a portable music player, an embedded computer, an AR headset, a VR headset, or any other computer system.

Generally, the processor 502 may include any suitable special-purpose or general-purpose computer, computing entity, or processing device including various computer hardware or software modules and may be configured to execute instructions stored on any applicable computer-readable storage media. For example, the processor 502 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data, or any combination thereof. In some embodiments, the processor 502 may interpret and/or execute program instructions and/or process data stored in the memory 504 and/or the file system 506. In some embodiments, the processor 502 may fetch program instructions from the file system 506 and load the program instructions into the memory 504. After the program instructions are loaded into the memory 504, the processor 502 may execute the program instructions. In some embodiments, the instructions may include the processor 502 performing one or more blocks of the method 600 of FIGS. 6A-6E.

The memory 504 and the file system 506 may include computer-readable storage media for carrying or having stored thereon computer-executable instructions or data structures. Such computer-readable storage media may be any available non-transitory media that may be accessed by a general-purpose or special-purpose computer, such as the processor 502. By way of example, and not limitation, such computer-readable storage media may include non-transitory computer-readable storage media including Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage media which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 502 to perform a certain operation or group of operations, such as one or more blocks of the method 600 of FIGS. 6A-6E. These computer-executable instructions may be included, for example, in the operating system 510, in one or more applications, such as the AR module 514, or in some combination thereof.

The communication unit 508 may include any component, device, system, or combination thereof configured to transmit or receive information over a network, such as the network 110 of FIG. 1. In some embodiments, the communication unit 508 may communicate with other devices at other locations, the same location, or even other components within the same system. For example, the communication unit 508 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, a cellular communication device, etc.), and/or the like. The communication unit 508 may permit data to be exchanged with a network and/or any other devices or systems, such as those described in the present disclosure.

The operating system 510 may be configured to manage hardware and software resources of the computer system 500 and may be configured to provide common services for the computer system 500.

The user interface 512 may include any device configured to allow a user to interface with the computer system 500. For example, the user interface 512 may include a display, such as an LCD, LED, or other display, such as an AR lens, that is configured to present video, text, application user interfaces, and other data as directed by the processor 502. The user interface 512 may further include a mouse, a track pad, a keyboard, a touchscreen, volume controls, other buttons, a speaker, a microphone, a camera, any peripheral device, or other input or output device. The user interface 512 may receive input from a user and provide the input to the processor 502. Similarly, the user interface 512 may present output to a user.

The AR module 514 may be one or more computer-readable instructions stored on one or more non-transitory computer-readable media, such as the memory 504 or the file system 506, that, when executed by the processor 502, is configured to perform one or more methods, such as one or more of the blocks of the method 600 of FIGS. 6A-6E. In some embodiments, the AR module 514 may be part of the operating system 510 or may be part of an application of the computer system 500, or may be some combination thereof.

Modifications, additions, or omissions may be made to the computer system 500 without departing from the scope of the present disclosure. For example, although each is illustrated as a single component in FIG. 5, any of the components 502-514 of the computer system 500 may include multiple similar components that function collectively and are communicatively coupled. Further, although illustrated as a single computer system, it is understood that the computer system 500 may include multiple physical or virtual computer systems that are networked together, such as in a cloud computing environment, a multitenancy environment, or a virtualization environment.

FIGS. 6A-6E are a flowchart of an example method 600 for augmenting views of a patient with 3D data. The method 600 may be performed, in some embodiments, by a device or system, such as by the AR module 514 of FIG. 5 executing on the AR headset 108 and/or on the server 112 of FIG. 1. In these and other embodiments, the method 600 may be performed by one or more processors based on one or more computer-readable instructions stored on one or more non-transitory computer-readable media. The method 600 will now be described in connection with FIGS. 1, 2A-2F, 3, 4A-4B, 5, and 6A-6E. Although the method 600 is described below as being performed by an AR headset, it is understood that the method 600 may alternatively be performed by another computer system or combination of computer systems.

At block 602, an AR headset may identify 3D data for a patient. For example, the AR headset 108 of FIG. 1 may identify, at block 602, 3D data for the patient 106.

In some embodiments, 3D data for the patient 106 of FIG. 1 may be captured or generated using one or more methods, either in real-time while the patient 106 is in the environment 100 and/or prior to the patient 106 entering the environment 100. For example, some of the 3D data may be obtained prior to the patient 106 entering the environment 100, and then the 3D data may be augmented with additional 3D data that is obtained in real-time while the patient 106 in in the environment 100. For example, 3D data of the patient 106 may include, but is not limited to, MRI images, Computerized Tomography (CT) scan images, X-ray images, Positron Emission Tomography (PET) images, ultrasound images, fluorescence images, Infrared Thermography (IRT) images, or Single-Photon Emission Computed Tomography (SPECT) scan image, or some combination thereof. Any of these images may be in the form of still images or video images. For example, the method 600 may employ still X-ray images of the skeletal system of the patient 106 (as illustrated in FIG. 1). In another example, the method 600 may employ video images of an ultrasound of a beating heart of the patient 106. In another example, the method 600 may be capable of toggling between a still image of the heart and a real-time video of the heart beating.

Although obtained using a variety of different methods, 3D data for a patient may, in some embodiments, include an outer layer of the patient and multiple inner layers of the patient. For example, the outer layer of the patient 106 of FIG. 1 may include the skin 106a of the patient 106 and/or the clothing 107 worn by the patient 106 in FIG. 1. In another example, the outer layer of a cadaver may be a tissue layer other than skin, such as a layer of muscle or fat, where the skin has been removed from the cadaver. The inner layers of the patient 106 may include, but are not limited to, interior bones 106b (as illustrated in FIG. 1), muscles, organs, or fluids of the patient 106. 3D data may include a 2D image, such as an X-ray image, because when the 2D image is projected into a 3D space the 2D image has 3D significance. For example, 3D data for the patient 106 may include a 2D X-ray image that may be projected onto the skin 106a or the clothing 107 of the patient 106. 3D data may also include a time element, which is sometimes referred to as four-dimensional (4D) data. For example, 3D data may include video that includes not only 3D images, but also include 3D images changing over time. The multiple inner layers may be layers that go all the way through the patient 106, or may be layers that only go to a certain partial depth into the patient 106. For example, some forms of 3D data, such as 3D data derived from a millimeter wave scanner, may only be configured to reveal items stored between the outer clothing and the skin of a patient. The 3D data may additionally or alternatively be data that only generally corresponds to the patient 106, instead of specifically corresponding to the patient 106, such as 3D data derived from a preset anatomy atlas. The 3D data may also be a combination of various types of 3D data.

In some embodiments, care may be taken to position the patient 106 of FIG. 1 on the operating table 103 in the same relative position and/or orientation that the patient 106 was in when the 3D data was captured. Alternatively, when the patient 106 is positioned in a different position and/or orientation on the operating table 103 than the patient 106 was in when the 3D data was captured or generated, the AR headset 108 may deform the 3D data to match the different position and/or orientation of the patient 106.

At block 604, an AR headset may determine virtual morphometric measurements of the outer layer of the patient from the 3D data. For example, the AR headset 108 of FIG. 1 may determine, at block 604, virtual morphometric measurements of the outer layer of the patient 106 from the 3D data. The determining of these virtual morphometric measurements may involve the AR headset 108 analyzing the 3D data in order to determine the size and shape of the outer layer of the patient from the 3D data. In some embodiments, the virtual morphometric measurements of the outer layer may involve generating a point cloud of the outer layer that represents the size and shape of the outer layer. For example, where the outer layer is represented by triangles or other polygonal shapes, the point cloud may include some or all of the vertices of the polygonal shapes.

At block 606, an AR headset may register a real-time position of the outer layer of the patient in a 3D space. For example, the AR headset 108 of FIG. 1 may register, at block 606, a real-time position of the skin 106a and clothing 107 of the patient 106 in the 3D space 102. In some embodiments, the AR headset 108 may include one or more sensors that are configured to map the 3D space 102, and map the real-time position of the outer layer of the patient 106 within the 3D space 102. These sensors may include, but are not limited to, infrared sensors, sound sensors, photographic sensors, fluoroscopy sensors, accelerometers, gyroscopes, or magnetometers.

At block 608, an AR headset may determine real-time morphometric measurements of the outer layer of the patient. For example, the AR headset 108 of FIG. 1 may determine, at block 608, real-time morphometric measurements of the skin 106a and clothing 107 of the patient 106. In some embodiments, the sensors employed in the registration at block 606 may also be employed to determine the real-time size and shape of the skin 106a and clothing 107 of the patient 106. In some embodiments, this may involve generating a point cloud of the skin 106a and clothing 107 of the patient 106 that represents the size and shape of the skin 106a and clothing 107.

At block 610, an AR headset may automatically register the position of the outer layer of the patient from the 3D data to align with the registered real-time position of the outer layer of the patient in the 3D space. For example, the AR headset 108 of FIG. 1 may automatically register, at block 610, the position of the outer layer of the patient 106 from the 3D data to align with the registered real-time position of the skin 106a and clothing 107 of the patient 106 in the 3D space 102. In some embodiments, this automatic registration may include automatically aligning the point cloud generated at block 604 with the point cloud generated at block 608 using point set registration. The automatic registration at block 610 may be less time consuming, less cumbersome, and less error-prone than manual methods of aligning an outer layer of a patient from 3D data with a real-time outer layer of the patient. Further, in some embodiments, the block 610 may be performed without using any non-anatomical fiducial, which may avoid the time consuming, cumbersome, and inaccurate placement of non-anatomical fiducials.

At block 612, an AR headset may display one of the inner layers of the patient from the 3D data projected onto real-time views of the outer layer of the patient. For example, the AR headset 108 of FIG. 1 may display, at block 612, the bones 106b of the patient 106 from the 3D data projected onto real-time views of the skin 106a and clothing 107 of the patient 106. In another example, a CT scan image of the brain of the patient is projected onto the top of the head of the patient in FIGS. 2B and 2C, or onto the side of the head of the patient in FIG. 2E.

At block 614, an AR headset may generate a confidence score that the automatic registration is correct and, at block 616, an AR headset may present the confidence score to a user. For example, the AR headset 108 of FIG. 1 may generate, at block 614, a confidence score that the automatic registration that was performed at block 612 is correct and present the confidence score to the user 104 visually, audibly, or in some other presentation format. In some embodiments, the AR headset 108 may generate this confidence score as part of the point set registration performed at block 612. For example, the confidence score may be a score between 0% and 100% indicating the level of confidence that the outer layer of the 3D data matches the outer layer of the patient 106. Where the confidence score is relatively high, the user 104 may proceed with training, research, diagnosis, or treatment on the patient 106 using the AR headset 108 with confidence that the 3D data being projected onto the patient 106 does, in reality, correspond to the patient 106. On the other hand, where the confidence score is relatively low, the user 104 may halt any training, research, diagnosis, or treatment on the patient 106 using the AR headset 108 because there may be legitimate doubts as to whether the 3D data being projected onto the patient 106 does, in reality, correspond to the patient 106.

At block 618, an AR headset may determine real-time morphometric measurements of an object prior to insertion of the object into the patient through the outer layer of the patient. For example, the AR headset 108 of FIG. 1 may determine, at block 618, real-time morphometric measurements of the object 118 prior to insertion of the object 118 into the patient 106 through the outer layer of the patient 106. In some embodiments, the determination at block 618 may be performed in a manner similar to the determination at block 608. In other embodiments, especially for a standard object, such as a standard medical instrument, the determination at block 618 may be performed by accessing morphometric measurements of the standard object found in design documents for the standard object.

At block 622, an AR headset may track a real-time position of the object in the 3D space with respect to the registered positions of the outer layer of the patient in the 3D space and with respect to the registered position of the outer layer of the patient from the 3D data. For example, the AR headset 108 of FIG. 1 may automatically track, at block 622, the real-time position of the object 118 in the 3D space 102 with respect to the registered position of the skin 106a and the clothing 107 of the patient 106 in the 3D space 102 and with respect to the registered position of the outer layer of the patient 106 from the 3D data.

At block 624, while a portion of the object is inserted into the patient through the outer layer of the patient, an AR headset may display a virtual portion of the object projected into the projected inner layer of the patient from the 3D data. For example, while a portion of the object 118 of FIG. 1 is inserted into the patient 106 through the clothing 107 of the patient 106, the AR headset 108 may display a virtual inserted portion 118b of the object 118 projected into the projected bones 106b of the patient 106 from the 3D data.

At block 626, an AR headset may display a virtual spatial difference box projected onto real-time views of the patient. For example, the AR headset 108 of FIG. 1 may display, at block 626, the virtual spatial difference box 116 projected onto real-time views of the patient 106. In some embodiments, the virtual spatial difference box 116 may confine within a volume of the virtual spatial difference box 116 the projected inner layer of the patient 106 from the 3D data, such as the projected bones 106b of FIG. 1.

At block 628, an AR headset may generate a virtual user interface that includes options for altering the display of the projected inner layer of the patient from the 3D data. For example, the AR headset 108 of FIG. 1 may generate, at block 628, the virtual user interface 114 that includes options for altering the display of the projected bones 106b of the patient 106 from the 3D data.

At block 630, an AR headset may display the virtual user interface projected onto realtime views while a focal orientation of the AR headset is not focused on the patient. For example, the AR headset 108 of FIG. 1 may display, at block 630, the virtual user interface 114 projected onto real-time views while the focal orientation 120 of the AR headset 108 is not focused on the patient 106.

At block 632, an AR headset may hide the virtual user interface while the focal orientation of the AR headset is focused on the patient. For example, the AR headset 108 of FIG. 1 may hide, at block 632, the virtual user interface 114 while the focal orientation 120 of the AR headset 108 is focused on the patient 106. In some embodiments, blocks 630 and 632 may avoid the virtual user interface 114 from obstructing any view of the patient 106.

At block 634, an AR headset may determine a real-time distance of the patient from the AR headset. For example, the AR headset 108 of FIG. 1 may determine, at block 634, the realtime distance D1 of the patient 106 from the AR headset 108. This real-time distance D1 may be, for example, the real-time distance to the center of the patient 106, to the center of an area of focus of the patient 106, to a slice of the 3D data currently being viewed on the patient 106, or some other point or general area on the patient 106.

At block 636, an AR headset may update, in real-time, the display of the virtual user interface to cause the virtual user interface to be continually positioned at a focal distance from the AR headset that is about equal to the real-time distance of the patient from the AR headset. For example, the AR headset 108 of FIG. 1 may update, in real-time, at block 636, the display of the virtual user interface 114 to cause the virtual user interface 114 to be continually positioned at a focal distance D2 from the AR headset 108 that is about equal to the real-time distance DI of the patient 106 from the AR headset 108. This focal distance D2 may be comfortable for the user 104 because it may avoid the user 104 having to change the focus of his eyes when shifting his focus between the patient 106 and the virtual user interface 114.

At block 638, an AR headset may update, in real-time, the display of the virtual user interface to cause the virtual user interface to continually be oriented perpendicularly to the focal orientation of the AR headset. For example, the AR headset 108 of FIG. 1 may update, in realtime, at block 638, the display of the virtual user interface 114 to cause the virtual user interface 114 to continually be oriented perpendicularly to the focal orientation 120 of the AR headset 108. Where the virtual user interface 114 is positioned above the AR headset 108, as disclosed in FIG. 1, orienting the virtual user interface 114 perpendicularly to the AR headset 108 may cause the top of the virtual user interface 114 to be tilted slightly downward toward the AR headset 108, as disclosed in FIG. 1. This orientation may be comfortable for the user 104 because it may cause the virtual user interface 114 to constantly face the user 104 head-on regardless of the current focal orientation 120 of the AR headset 108 and regardless of where the user 104 is standing in the 3D space 102.

At block 640, an AR headset may display a virtual cursor projected onto real-time views and/or onto the virtual user interface while a focal orientation of the AR headset is not focused on the patient. For example, the AR headset 108 of FIG. 1 may display, at block 640, the virtual cursor 122 projected onto real-time views and/or onto the virtual user interface 114 while the focal orientation 120 of the AR headset 108 is not focused on the patient 106.

At block 642, an AR headset may hide the virtual cursor while a focal orientation of the AR headset is focused on the patient. For example, the AR headset 108 of FIG. I may hide, at block 642, the virtual cursor 122 while the focal orientation 120 of the AR headset 108 is focused on the patient 106. In some embodiments, blocks 640 and 642 may avoid the virtual cursor 122 from obstructing any view of the patient 106. In some embodiment, the AR headset 108 of FIG. 1 may only selectively hide, at block 642, the virtual cursor 122 while the focal orientation 120 of the AR headset 108 is focused on the patient 106. In these embodiments, there may be situations where the user 104 may desire to use the virtual cursor 122 while the focal orientation 120 of the AR headset 108 is focused on the patient 106, such as when the user 104 is using an annotation tool to annotate the view of the patient 106 and/or to annotate the projected 3D data (e.g., a crosshairs annotation that may remain projected on the patient 106 even when other 3D data has been hidden, for example, to assist in keeping track of a location of interest during surgery), or when the user 104 is using a measuring tool to make a measurement of the view of the patient 106 and/or to measure the projected 3D data.

In some embodiments, the method 600 may accomplish automatic alignment between 3D data of a patient and the actual patient. Further, this automatic alignment may be accomplished without manual alignment and/or without manual placement of non-anatomical fiducials, thus achieving automatic alignment more easily and more accurately that conventional forms of manual alignment.

Although the blocks of the method 600 are illustrated in FIGS. 6A-6E as discrete blocks, various blocks may be divided into additional blocks, combined into fewer blocks, reordered, expanded, or eliminated, depending on the desired implementation. For example, in some embodiments, blocks 602-612 may be performed without performing any of blocks 614-642. Further, in some embodiments, only blocks 602 and 612 may be performed, without blocks 604-610, such as where the registration and alignment between the patient and the 3D data is performed manually instead of automatically, in connection with any of blocks 614-616, 618-624, 626, or 628-642. Further, in some embodiments, blocks 628-632 may be performed without blocks 634-642. Also, in some embodiments, blocks 628-636 may be performed without blocks 638-642, blocks 628-632 and 638 may be performed without blocks 634-636 and 640-642, or blocks 628-632 and 640-642 may be performed without block 634-638. Further, in some embodiments, any of the blocks 614-642 may be performed in parallel.

In another example, the method 600 may further include dealing with the problem of automatic registration either before or after a patient is covered in surgical draping. For example, block 610 may be performed prior to covering a patient in surgical draping, and then the 3D data may be projected at block 612 onto the surgical draping. However, if block 610 is performed after a patient is covered in surgical draping, the method 600 may be modified to deal with the problem of the surgical draping obscuring a suitable outer layer of the patient. One such modification to the method 600 may include employing surgical draping that is sufficiently transparent that the AR headset can penetrate the surgical draping and find a more suitable outer layer of the patient. Another such modification may include placing visual markers on the outer layer of the patient in positions (such as in a particular pattern) that will remain visible after surgical draping and that can be noted during block 612. Then, even when large portions of the patient are covered in relatively opaque surgical draping, as long as the visual markers are still visible, an automatic re-registration can be performed using the visual markers as reference points. Another such modification includes placing extra-visual markers on the outer layer or the patient, or possibly inside the patient, in positions (such as in a particular pattern) that will not remain visible after surgical draping but that can be noted during block 612, either because they are visible during block 612 or because they are sensed by a sensor during block 612. These extra-visual markers may be made of a material that can be detected underneath the surgical draping by sensors in the AR headset, even though the extra-visual makers are not visible to the AR headset. For example, a metal detector sensor may detect metallic extra-visual markers (such as metallic mesh markers or a metallic marker inserted under the skin or into a body cavity), an infrared sensor may detect infrared-detectible extra-visual markers, a magnetic detector sensor may detect magnetic-field-emitting extra-visual markers, or a radio frequency detector may detect radio-frequency-emitting extra-visual markers. Then, even when large portions of the patient are covered in relatively opaque surgical draping, as long as the sensors in the AR headset are able to detect the positions of the extra-visual markers underneath the surgical draping, an automatic re-registration can be performed using the extra-visual markers as reference points.

Further, it is understood that the method 600 may improve the functioning of an AR system itself and may improve the field of AR. For example, the functioning of the AR headset 108 of FIG. 1 may itself be improved by the method 600 by automatically registering a virtual position of the outer layer of the patient 106 from the 3D data to align with the registered real-time position of the outer layer (e.g. skin 106a and clothing 107) of the patient 106 in the 3D space 102 using the virtual morphometric measurements and using the real-time morphometric measurements and, in some instances, without using any non-anatomical fiducial. This automatic registration may be performed more easily and more accurately than conventional AR systems which employ manual registration or registration using manual placement of non-anatomical fiducials.

As indicated above, the embodiments described herein may include the use of a special purpose or general purpose computer (e.g., the processor 502 of FIG. 5) including various computer hardware or software modules, as discussed in greater detail below. Further, as indicated above, embodiments described herein may be implemented using computer-readable media (e.g., the memory 504 or file system 506 of FIG. 5) for carrying or having computer-executable instructions or data structures stored thereon.

In some embodiments, the different components and modules described herein may be implemented as objects or processes that execute on a computing system (e.g., as separate threads). While some of the methods described herein are generally described as being implemented in software (stored on and/or executed by general purpose hardware), specific hardware implementations or a combination of software and specific hardware implementations are also possible and contemplated.

In accordance with common practice, the various features illustrated in the drawings may not be drawn to scale. The illustrations presented in the present disclosure are not meant to be actual views of any particular apparatus (e.g., device, system, etc.) or method, but are merely example representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, it is understood that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the summary, detailed description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

The foregoing description, for purpose of explanation, has been described with reference to specific embodiments. However, the illustrative discussions above are not intended to be exhaustive or to limit the invention as claimed to the precise forms disclosed. Many modifications and variations are possible in view of the above teachings. The embodiments were chosen and described to explain practical applications, to thereby enable others skilled in the art to utilize the invention as claimed and various embodiments with various modifications as may be suited to the particular use contemplated.

The invention claimed is:

1. A method for augmenting real-time, non-image actual views of a patient with three-dimensional (3D) image data, the method comprising:
   identifying 3D image data for the patient, the 3D image data including an outer layer of the patient or multiple inner layers of the patient; and
   displaying, in an augmented reality (AR) headset, one of the inner layers of the patient from the 3D image data projected onto real-time, non-image actual views of the outer layer of the patient, the projected inner layer of the patient from the 3D image data being confined within a volume of a virtual 3D shape, wherein a virtual user interface is provided for altering display of the 3D image data of the patient.

2. The method of claim 1, wherein the 3D image data is direct volume rendered.

3. The method of claim 1, wherein the virtual user interface displays a slice of the 3D image data instead of a volume of the 3D image data.

4. The method of claim 3, wherein the slice may be a three-dimensional (3D) slice.

5. The method of claim 3, wherein the slice may be a curved slice that follows a natural curve of an anatomical feature of the patient.

6. The method of claim 1, wherein the virtual user interface enables dragging a plane through the 3D image data to a location within the 3D image data, the plane displaying a slice of the 3D image data at the location of the plane within the 3D image data.

7. The method of claim 1, wherein the virtual user interface enables display of slices of the 3D image data including: axial slices, coronal slices, sagittal slices, and oblique slices.

8. The method of claim 1, wherein:
the virtual 3D shape is configured to be controlled to toggle between displaying and hiding lines of the virtual 3D shape; and
the virtual 3D shape is configured to be controlled to reposition two-dimensional (2D) slices and/or 3D slices of the projected inner layer of the patient from the 3D image data.

9. A method for augmenting real-time, non-image actual views of a patient with three-dimensional (3D) image data, the method comprising:
identifying 3D image data that is direct volume rendered for the patient, the 3D image data including an outer layer of the patient and multiple inner layers of the patient;
co-registering the 3D image data to real-time, non-image actual views of the outer layer of the patient; and
displaying, in an augmented reality (AR) headset, one of the inner layers of the patient from the 3D image data projected onto the real-time, non-image actual views of the outer layer of the patient, the projected inner layer of the patient from the 3D image data being confined within a volume of a virtual 3D shape, wherein a virtual user interface is provided for altering display of the projected inner layer of the patient from the 3D image data of the patient.

10. The method of claim 9, wherein the virtual 3D shape displays a slice of the 3D image data instead of a volume of the 3D image data.

11. The method of claim 10, wherein the slice may be a two-dimensional (2D) slice, three-dimensional (3D) slices, a curved slice, a curved slice that follows a natural curve of an anatomical feature, or a slice that has a depth, a height, and a width.

12. The method of claim 9, wherein the virtual user interface enables repositioning of the virtual 3D shape to a location overlapping at least a portion of the real-time, non-image actual views patient.

13. The method of claim 12, wherein the virtual 3D shape displays the 3D image data of the patient at the location of the virtual 3D shape.

14. The method as recited in claim 9, wherein:
the virtual 3D shape is a virtual box; and
the virtual box includes a top side, a bottom side, a left side, a right side, a front side, and a back side.

15. The method of claim 9, wherein:
the virtual 3D shape is configured to be controlled to toggle between displaying and hiding lines of the virtual 3D shape; and
the virtual 3D shape is configured to be controlled to reposition two-dimensional (2D) slices and/or 3D slices of the projected inner layer of the patient from the 3D image data.

16. The method of claim 15, wherein the virtual user interface provided for altering display of the projected inner layer of the patient from the 3D image data of the patient, and further comprises altering slices in the projected inner layer of the patient.

17. A method for augmenting real-time, non-image actual views of a patient with three-dimensional (3D) image data, the method comprising:
identifying 3D image data that is direct volume rendered for the patient, the 3D image data including an outer layer of the patient and multiple inner layers of the patient; and
displaying, in an augmented reality (AR) headset, one of the inner layers of the patient from the 3D image data projected onto real-time, non-image actual views of the outer layer of the patient, the projected inner layer of the patient from the 3D image data being confined within a volume of a virtual 3D shape, wherein a virtual user interface is provided for altering display of at least one slice of the projected inner layer of the patient from the 3D image data of the patient.

18. The method of claim 17, wherein the at least one slice may be a two-dimensional (2D) slice, three-dimensional (3D) slice, a curved slice, a curved slice that follows a natural curve of an anatomical feature, or a slice that has a depth, a height and a width.

19. The method of claim 17, wherein the virtual user interface enables dragging the 3D image data in a direction of a user.

20. The method of claim 17, wherein the virtual user interface enables repositioning of a slice of the 3D image data.

21. The method of claim 17, wherein the virtual user interface enables display of different slices of the 3D image data including at least one of: axial slices, coronal slices, sagittal slices, or oblique slices.

22. A method for augmenting real-time, non-image actual views of a patient with three-dimensional (3D) image data, the method comprising:
identifying 3D image data for the patient, the 3D image data including an outer layer of the patient or multiple inner layers of the patient; and
displaying, in an augmented reality (AR) headset, one of the inner layers of the patient from the 3D image data projected onto real-time, non-image actual views of the outer layer of the patient, the projected inner layer of the patient from the 3D image data being confined within a volume of a virtual 3D shape, wherein the 3D image data is direct volume rendered and a virtual user interface is provided for altering display of the 3D image data of the patient.

* * * * *